(12) United States Patent
Bazemore et al.

(10) Patent No.: US 10,816,519 B1
(45) Date of Patent: Oct. 27, 2020

(54) SYSTEMS AND METHODS FOR ANALYZING ODORS

(71) Applicant: VOLATILE ANALYSIS CORPORATION, Grant, AL (US)

(72) Inventors: Russell A. Bazemore, Grant, AL (US); Katherine Bazemore, Grant, AL (US); Chris P. Christenson, Sequin, TX (US); Mitchell R. White, Round Rock, TX (US)

(73) Assignee: Volatile Analysis Corporation, Grant, AL (US)

( * ) Notice: Subject to any disclaimer, the term of this patent is extended or adjusted under 35 U.S.C. 154(b) by 184 days.

(21) Appl. No.: 16/039,140

(22) Filed: Jul. 18, 2018

Related U.S. Application Data

(60) Provisional application No. 62/534,069, filed on Jul. 18, 2017.

(51) Int. Cl.
*G01N 30/00* (2006.01)
*G01N 30/88* (2006.01)
*G01N 30/60* (2006.01)
*G01N 30/02* (2006.01)

(52) U.S. Cl.
CPC ............. *G01N 30/88* (2013.01); *G01N 30/60* (2013.01); *G01N 2030/025* (2013.01)

(58) Field of Classification Search
CPC .. G01N 30/88; G01N 30/60; G01N 2030/025; G01N 29/022; G01N 5/02; G01N 27/12; G01N 33/0001; G01N 1/2273; G01N 33/0006; G01N 7/00
See application file for complete search history.

(56) References Cited

U.S. PATENT DOCUMENTS

| | | | | |
|---|---|---|---|---|
| 6,360,584 | B1* | 3/2002 | Okubo | G01N 33/0031 205/787 |
| 7,860,893 | B2* | 12/2010 | Ouzounian | G16H 50/80 707/796 |
| 8,190,443 | B1* | 5/2012 | Ouzounian | G16H 50/80 705/1.1 |
| 2002/0000115 | A1* | 1/2002 | Nakano | G01N 33/0047 73/23.34 |
| 2007/0077204 | A1* | 4/2007 | Devanand | A61K 49/00 424/9.2 |
| 2007/0089484 | A1 | 4/2007 | Bailey et al. | |

(Continued)

*Primary Examiner* — Francis C Gray
(74) *Attorney, Agent, or Firm* — Maynard Cooper & Gale, P.C.; Jon E. Holland

(57) ABSTRACT

An odor analysis system is provided to analyze odors present at a particular location and perform a preliminary identification of the odors while still at the location. The odor analysis system can have an odor processing device that collects samples of the odors and provides a series of odor notes to a user. The odor notes can be based on the separated and concentrated molecules in the collected sample. The odor analysis system can also include a handheld computing device with a user interface that permits the user to enter information, both verbally and through touch input, about the series of odor notes provided by the odor processing device. The information entered by the user about the series of odor notes along with retention index information about the series of odor notes can be to perform a preliminarily identification of the molecules associated with the odors present at the location.

8 Claims, 7 Drawing Sheets

(56) References Cited

U.S. PATENT DOCUMENTS

| | | |
|---|---|---|
| 2007/0266858 A1 | 11/2007 | Alm et al. |
| 2013/0025347 A1 | 1/2013 | Rhodes et al. |
| 2014/0047900 A1 | 2/2014 | Amirav et al. |
| 2015/0330953 A1 | 11/2015 | McCauley et al. |
| 2017/0089873 A1* | 3/2017 | Neynavaee ........ G01N 33/0001 |
| 2017/0199159 A1* | 7/2017 | Kuroki ............... G01N 33/0031 |
| 2017/0290541 A1* | 10/2017 | Albers ................. A61B 5/7475 |

* cited by examiner

SYSTEMS AND METHODS FOR ANALYZING ODORS

CROSS REFERENCE TO RELATED APPLICATION

This application claims the benefit of U.S. Provisional Application No. 62/534,069, filed Jul. 18, 2017 and entitled "Systems and Methods for Analyzing Odors," which application is hereby incorporated by reference in its entirety.

BACKGROUND

The present application generally relates to systems and methods for analyzing odors at the location where the odors are present.

The presence of an unfamiliar and/or unpleasant odor in area may be a source of annoyance for people that are living or working in the area. In some cases, the presence of the odor may be indicative of a safety hazard to the people in that area. In order to take action to remediate (and/or prevent) the presence of the odor, and possibly the safety hazard associated with the odor, an identification of the odor has to occur so that the source of the odor can be determined and appropriate remediation steps taken to eliminate the odor. However, the identification of the odor in an area can be difficult because the odor may only be intermittently present in the area (e.g., the odor is detectable for a certain time period and then is undetectable for another time period) and/or diluted by the surrounding conditions in the area.

One technique for identifying an odor in an area can involve the capturing of samples in the area and then taking the samples to a laboratory for subsequent analysis of the samples and identification of the odors. One drawback to this technique is that it is difficult for the person capturing the sample to ensure that an appropriate sample has been captured (i.e., a sample with sufficient odorous molecules from the source of the odor to perform a successful analysis). Another drawback to this technique for identifying odors is that it can take a substantial amount of time (e.g., days or weeks) for the identification of the odors to occur. Improved techniques for analyzing odors more reliably and quickly are generally desired.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Figure 1:
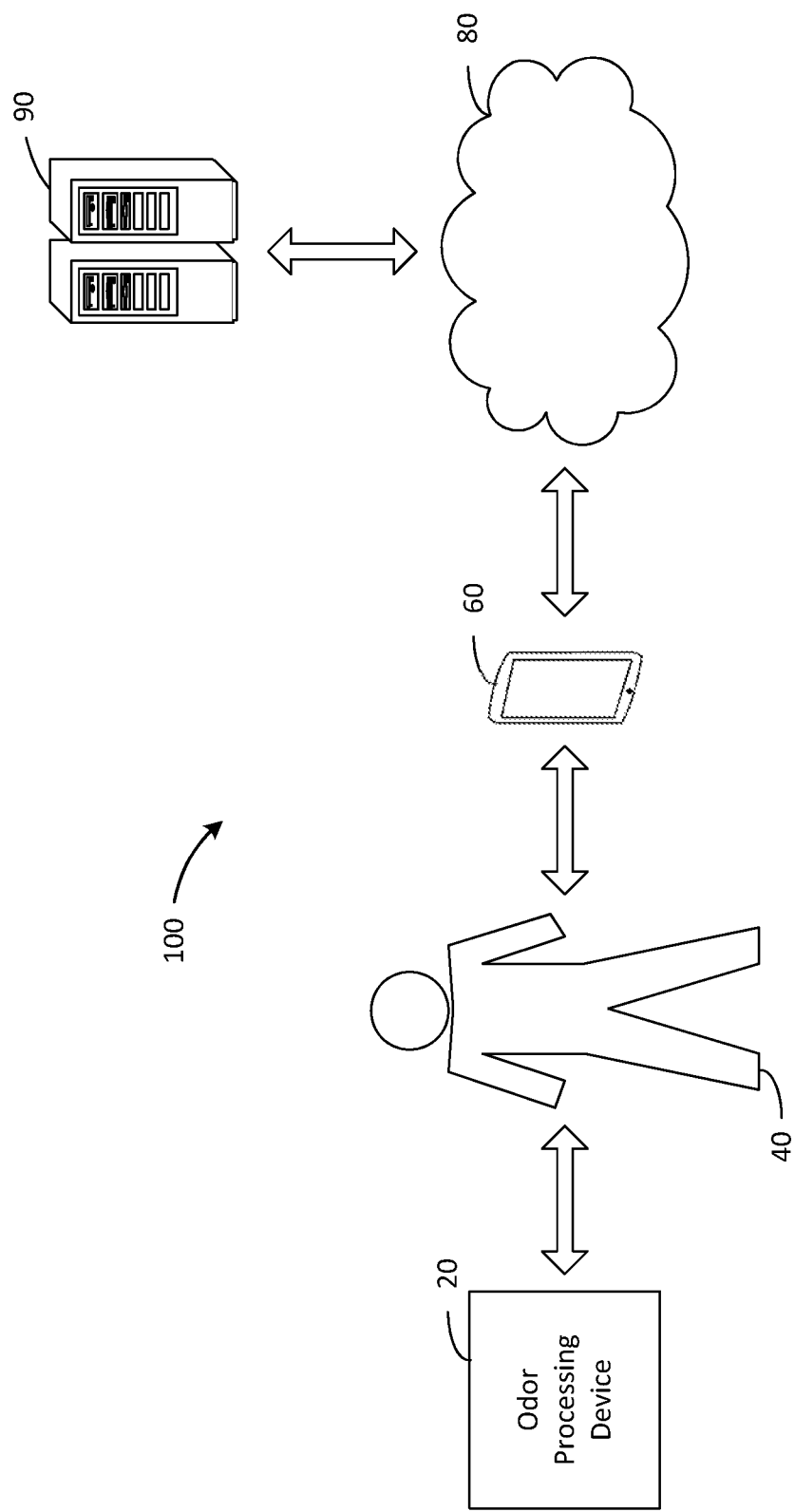
FIG. 1 schematically shows an embodiment of a system in accordance with the present disclosure.

The present disclosure generally pertains to an odor analysis system to analyze odors present at a particular location and perform a preliminary identification of the odors while still at the location. The odor analysis system can have a mobile odor processing device that collects samples of the odors and provides a series of odor notes to a user. The odor notes can be based on the separated and concentrated molecules in the collected sample. The odor analysis system can also include a hand-held computing device with a user interface that permits the user to enter olfactory information about the series of odor notes provided by the odor processing device. The olfactory information (e.g., intensity, duration and odor descriptors) entered by the user about the series of odor notes along with retention index information about the series of odor notes can then be used to perform a preliminarily identification of the molecules associated with the odors present at the location. The preliminary identification of the molecules can then be used to confirm that the collected samples are suitable for subsequent analysis by a laboratory. The laboratory can then perform additional analysis on the collected samples in order to confirm the preliminary identification of the molecules.

The odor processing device can include a standalone, portable, odor measuring/characterizing instrument that extracts and concentrates molecules associated with odors and other volatile chemicals in the surrounding environment. The odor processing device can separate the molecules and provide the separated molecules to the user as the series of odor notes. In other words, the odor processing device can be a portable instrument that can be carried into an environment (e.g., inside an industrial building, farm, construction site, etc.) to concentrate the chemicals (and molecules) responsible for odors (and all other volatile chemicals present in the air) and then provide the capability for a user to detect the odorous chemicals by olfaction.

The odor processing device can have multiple sample collecting devices (e.g., sample traps) that can collect samples of the odors in the surrounding environment. Each of the sample collecting devices can include a sorbent material that extracts and concentrates odorous components, volatile, semi-volatile and non-volatile chemicals, and hazardous volatile organic compounds from the atmosphere surrounding the odor processing device. The odor processing device can then desorb and separate the molecules from the sorbent material using a gas chromatograph or via other suitable devices or techniques for desorbing and separating molecules from a sorbent material. In some embodiments, the odor processing device may incorporate a mass spectrometer (or other detector) to deliver additional information about the collected molecules.

The user can then enter olfactory information about the series of odor notes provided by the odor processing device using the user interface of the hand-held computing device. The user interface enables the user to enter information relating to the time, intensity, duration, and olfactometry perception of the odor notes via cross-modal matching. In one embodiment, a user (e.g., a trained odor judge) sniffs the separated, concentrated molecules forming the series of odor notes and describes the odor and rates the odor intensity utilizing time-intensity olfactometry based on cross-modal matching and odor intensity-distance perception. The olfactory information can then be recorded electronically (e.g., stored in the hand-held computing device) and then presented in graphical form for data interpretation (e.g., displayed on the hand-held computing device). The graphical display can be important to indicate which molecules may be responsible for the odor. The hand-held computing device can then calculate a retention index for the molecules and use the retention index and the other olfactory information to identify the specific molecules. The hand-held computing device can obtain information over the Internet from reference databases that include information that specifically identifies molecules by retention index and other olfactory information in order to identify the molecules by the calculated retention index and other olfaction information entered by the user.

Once the identified molecules are confirmed as being from a good sample, one of the sample collecting devices that was not used to provide the series of odor notes (e.g., an unprocessed sample collecting device) can be provided to a laboratory for further analysis. In the laboratory, the chemicals in the collected sample may then be identified by desorbing the sorbent material from the sample using appropriate techniques including thermal desorption, solvent desorption, chemical desorption, desorption by exposure to energy sources or other suitable methods. The extracted chemicals can then be analyzed by any analytical instrumentation including gas chromatography and high performance liquid chromatography, and any detector including any form of mass spectrometry (including SIFT (selected ion flow tube)), flame ionization, UV (ultraviolet), IR (infrared), or a biological or electronic nose. The results from the laboratory analysis can then be compared to the identified molecules from the hand-held device to confirm the identification of molecules by the hand-held device.

FIG. 1 shows an embodiment of a system that can be used to analyze and identify odors at the location where the odors are present. The system 100 can include an odor processing device 20 to collect odors and provide a series of odor notes to a user 40. The user 40 can sniff the series of odor notes and enter olfactory information regarding the series of odor notes into a hand-held computing device 60. The hand-held computing device 60 can communicate over a network 80 with a server computer 90 to obtain information to identify the molecules associated with the series of odor notes based with the information entered into the hand-held computing device 60 and other information generated by the hand-held computing device. In one embodiment, the network 80 can be the Internet and use transmission control protocol/Internet protocol (TCP/IP) for communication. However, in other embodiments, the network 80 may be an Intranet, a local area network (LAN) or a wide area network (WAN), or any other type of communication network using one or more communication protocols. The server computers 90 can store information correlating a specific molecule to one or more characteristics of the molecule (e.g., a retention index and corresponding olfactory information). In one embodiment, the information stored by the server computers 90 regarding the molecules may be organized into one or more databases and/or tables.

Figure 2:
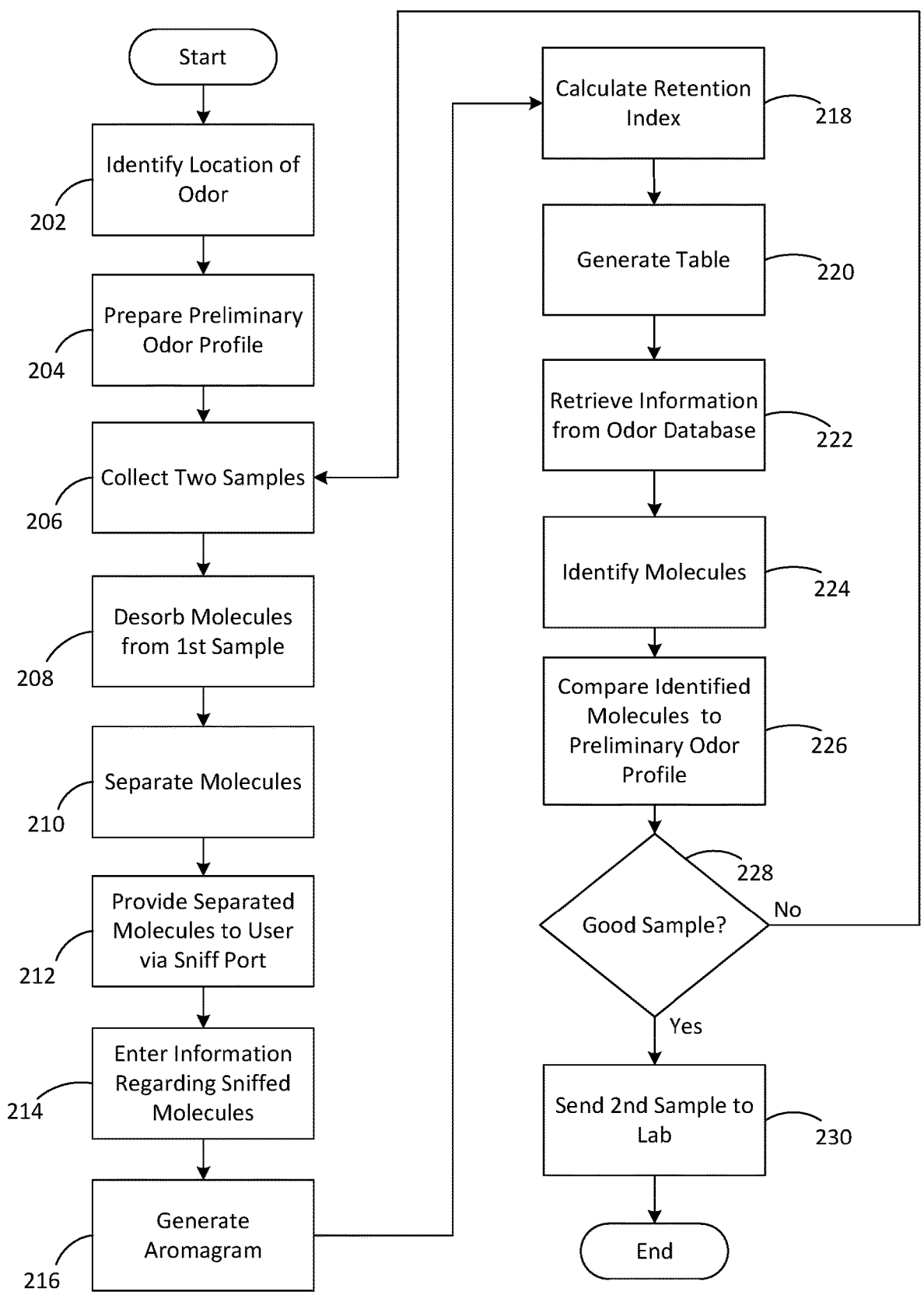
FIG. 2 is a flowchart showing an embodiment of a process for using the system of FIG. 1.

FIG. 2 shows an embodiment of a process using the system 100 for the identification and verification of molecules responsible for an odor at a particular location. The process begins with a user 40 (e.g., an odor judge) bringing the system 100 to a site having an odor problem and identifying the location of the odor (step 202). In one embodiment, the user 40 can inspect the site to determine a specific location at the site where the odor is believed to be the strongest or most prevalent. Once the user 40 has determined a location for the odor, the user 40 can use the hand-held device 60 to prepare and store a preliminary odor profile for the odor (step 204). In one embodiment, the preliminary odor profile can include one or more character descriptors (provided by the user 40) for the aromas sniffed by the user 40 (e.g., sweet, sulfury, fruity, musty, foul, rotten, oily, onion, almond, earthy, sharp, floral, grassy, etc.) and any candidate molecules the user 40 believes may be present at the location based on the user's sniffing of the aromas at the location. After the user 40 has prepared and stored the preliminary odor profile in the hand-held device 60, the user 40 can position the odor processing device 20 at the location.

The odor processing device 20 can collect two (or more) samples of the odors at the location (step 206). In one embodiment, the odor processing device 20 can collect samples by flowing air from the environment at the location and extracting and concentrating the molecules from the air into a sorbent material. Once the samples have been collected, the odor processing device 20 can desorb the molecules from the sorbent material of a first sample (step 208) and then separate the molecules (step 210). In one embodiment, the desorbing of the molecules from the sorbent material and the separation of the molecules can be performed by a gas chromatograph incorporated into the odor processing device 20. The separated molecules can then be provided to the user 40 as a series of odor notes at a sniff port of the odor processing device 20 (step 212).

Figure 3:
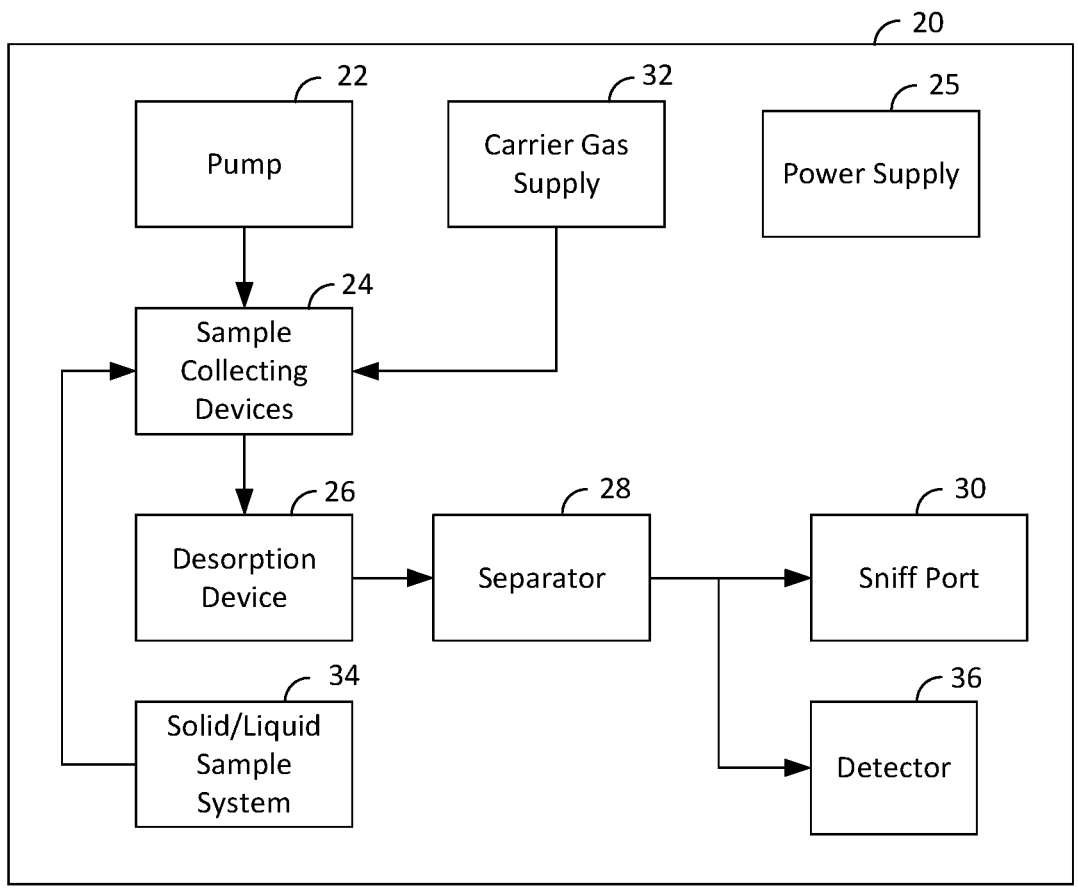
FIG. 3 shows a block diagram of an embodiment of an odor processing device from the system of FIG. 1.

FIG. 3 shows an embodiment of an odor processing device 20. The odor processing device can obtain samples by having a pump 22 draw outside air from the surrounding environment of the location into or over the surface of two or more sample collecting devices 24 (e.g., sample traps). The sample collecting devices 24 can include a sorbent material that is mounted on the exterior of a hollow tube (or cylinder) formed from metal (e.g., stainless steel), glass, ceramic or a glass or ceramic coated metal tube and maintained at an ambient temperature. In another embodiment, the sorbent material may also be positioned (e.g., packed) inside the hollow tube. In one embodiment, the sorbent material can be adhered to the exterior (and/or interior) surface of the hollow tube using a polymeric resin such as polydimethylsiloxane (PDMS) or other similar resin. However, in other embodiments, other techniques can be used for mounting the sorbent material on the hollow tube. The odor processing device 20 can include a housing (not shown) that secures the sample collecting devices 24 in position to collect the samples.

The sorbent material may include one or both of absorbent and adsorbent material. Regardless of which type of sorbent material is used, the sorbent material can extract and retain volatile, semi-volatile, and non-volatile molecules from the environment by absorption and adsorption. Forces and mechanisms responsible for the absorption and/or adsorption include Van der Waals forces, hydrogen bonding and/or polarity. In an embodiment, the sorbent material can include materials that do not have volatiles and are thermally stable, such as polydimethylsiloxane (PDMS). However, in other embodiments, the sorbent material can include, in addition to or in place of PDMS, one or more of the following: Tenax®, activated carbons made to various pore sizes (e.g., CarboPack™ or Carboxen®), zeolites, Carbowax™, polyethylene (particularly low crystallinity polyethylene), polypropylene, suitable acrylates (including blends and copolymers), cellulose, papers, silica gel, alumina, zeolites (particularly large pore volume zeolites) polystyrene templated absorbents, macroporous polymer beads, natural polymers (e.g., chitin or chitosan or their derivatives), cyclodextrins or other material that may be matched via Hansen solubility parameters. In further embodiments, the sorbent material layer 20 may also include polyvinyl acetate, polyisoprene, styrene-butadiene rubber (SBR), polybutylene, polyacrylate, polyglycol or polyurethane as well as other polymers that are known in the art, or may become known in the art. Softening agents such as microcrystalline wax may also be utilized to provide a softer, easy to mold sorbent material.

In one embodiment, the sorbent material can target specific chemicals (or molecules) or classes of chemicals (or molecules). In other words, the sorbent material can be selected such that the sorbent material is sensitive to (e.g., absorbs or adsorbs) or selects certain chemicals or classes of chemicals. For example, small fatty acids (e.g., smell of rancid butter) may be extracted and/or trapped by having an ion exchange surface on or in the sorbent material such that when the small fatty acid is absorbed by the sorbent material, the small fatty acid is held or fixed in place in the sorbent material. Similar techniques can be used to extract and trap aldehydes, ammonias, amines or other acids in other embodiments. In one embodiment, the selection of the sorbent material may be based on the Hansen solubility parameters of the target chemicals or odors.

In an embodiment, the sorbent material can have a sufficient volume of sorbent material to permit the sorbent material to extract and hold a sufficient amount of molecules to permit subsequent analysis. The volume of the sorbent material can be controlled based on the surface area of the sorbent material and the thickness of the sorbent material. The thickness of the sorbent material can be based on the surface area for the sorbent material, which is controlled by the size of the hollow tube, such that there is a sufficient volume of sorbent material. The surface area, thickness and total volume of the sorbent material can be optimized to permit the quick desorbing of the molecules from the sorbent material when energy is applied.

After an appropriate sample has been collected, a desorption device 26 can be used to desorb the molecules from the sorbent material of one of the sample collecting devices 24. In one embodiment, the sample collecting device 24 can be heated by the desorption device 26 to thermally desorb (or release) the molecules from the sorbent material. In one embodiment, the sorbent material of the sample collecting device 24 can be rapidly heated by conduction from a metal (e.g., the hollow tube used for mounting the sorbent material or a metal rod inserted in the hollow tube) that is heated by induction with electromagnetic waves in the frequency range of 100-400 kHz. In another embodiment, the temperature of the surrounding environment for the sample collecting device 24 can be raised (e.g., by placing the sample collecting device 24 in an oven) to raise the temperature of the sorbent material and release the molecules. The desorption device 26 may incorporate a thermocouple to monitor and maintain the temperature used for desorption. In a further embodiment, Peltier heating may be used to heat the sorbent material. Since the sorbent material may be heated rapidly due to a shallow depth of material and a large surface area in contact with the hollow tube, the differences in individual molecule releases from the sorbent material can be very small, which can result in all molecules desorbing from the sorbent material at the same time.

When the molecules release from the sorbent material, the molecules can be separated by separator 28 so that the molecules are not provided to the sniff port 30 and detector 36 at the same time and overload the user 40 and detector 36. When molecules release from the sorbent material, the molecules can be pushed by an inert gas or other carrier gas (e.g., nitrogen, argon, hydrogen or helium) from carrier gas supply 32 into the separator 28. In one embodiment, the separator 28 can be a piece of capillary column (e.g., a fused silica tube) that has coatings that force the molecules to interact with the coatings inside the column in order to affect the velocity at which the molecules traverse the column and reach the sniff port 30 and detector 36. The molecules can interact with the coatings inside the fused silica tube based on the molecule's and the coating's molecular size, polarity, hydrogen bonding, and other physical parameters. In one embodiment, the desorption device 26 and the separator 28 may be provided by a gas chromatograph that is incorporated in the odor processing device 20. The gas chromatograph may include an oven (e.g., a desorption device 26) that houses a gas chromatographic capillary column (e.g., a separator 28).

The sniff port 30 can be coupled to the separator 28 or to the split point with the detector 36 by a short length of capillary tubing that terminates into a nose cone. In one embodiment, the capillary tubing can be formed from inert methyl silicone or other stationary phase material and the nose cone may be formed from glass or other material. The nose cone may be heated independently from the separator 28. The detector 36 can be coupled to the split point with the sniff port 30 by capillary tubing similar to that used for the sniff port 30. In one embodiment, the detector 36 can be a mass spectrometer, infrared (IR), ultra violet (UV), flame photometric, diode array, or other chemical detector. Electric power for the detector 36 may be provided by power supply 25. In an embodiment, the length and diameter of the column in separator 28 can determine what split of molecules (e.g., 50%, 67%, etc.) goes to the sniff port 30 and what split of molecules (e.g., 50%, 33%, etc.) goes to the detector 36. While the embodiment of FIG. 3 shows a detector 36 coupled to the separator 28, it is to be understood that other embodiments of the odor processing device 20 may not include a detector 36 and the molecules from the separator 28 would be provided directly to the sniff port 30.

As an example, molecules released by desorption device 26 can be swept from the surface of the sorbent material into inert capillary column tubing (e.g., the separator 28) by an inert gas (e.g., nitrogen) or other carrier gas. As the molecules pass through the length of tubing (molecules in nitrogen carrier gas can be called effluent) the flow is split with part going through a length of tubing directed to the sniff port 30 where the user 40 sniffs the molecules. The remainder of effluent is directed to the detector 36 for analysis by the detector 36.

In an alternate embodiment, the molecules in the sorbent material can more slowly absorb energy via conduction from a metal tube that is being slowly heated by induction (or Peltier heater) while trapped in the sorbent material and can reach an energy state that breaks the bonds between the molecules and the sorbent material thereby releasing the molecule. The different and unique capacity at which different molecule functional groups absorb energy results in the molecules releasing from the sorbent material at different times, thereby removing the need for separator 28. In other words, the molecules may be thermally desorbed from the sorbent material with a slower ramp of temperature, thus eliminating the need for the separator 28 (e.g., gas chromatographic column).

In another embodiment, the sample collecting device 24 can be irradiated by electromagnetic energy, including tunable microwaves, from the desorption device 26. In one embodiment, the desorption device 26 can include a magnetron wave guide that provides tunable electromagnetic radiation for the purpose of desorbing molecules present in the sorbent material. If the sample collecting device 24 is to be irradiated by electromagnetic energy, the sorbent material can be mounted on a glass or ceramic tube (but not a metal tube). The molecules can desorb from the sorbent material by uniquely absorbing energy based on functional groups present in molecules, or by the sorbent material uniquely absorbing energy based on functional groups in the sorbent material and the molecules absorbing energy due to conduction. The molecules can absorb microwave energy while trapped in the sorbent material and can reach an energy state that breaks the bonds between the molecules and the sorbent material. In an embodiment, the molecules can absorb microwave energy at different levels than the sorbent material. The different and unique capacity at which different molecule functional groups absorb electromagnetic energy results in the molecules breaking free from the sorbent material at different times thereby removing the need for separator 28.

In still another embodiment, an electronic gate can be used for separator 28. In an electronic gate, electric current causes the molecules to align and form a barrier. By turning the current on and off, the barrier is closed or opened, thus establishing a passage for separated molecules to flow from the desorption device 26 to the sniff port 30 and detector 36.

Figure 4:
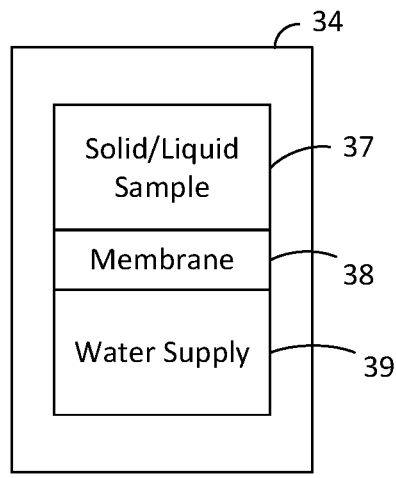
FIG. 4 shows a block diagram of an embodiment of a solid/liquid sample system from the odor processing device of FIG. 3.

In a further embodiment, a suspect odorous material that is from either a solid or liquid sample can be placed into the solid/liquid sample system 34 for extraction of the odorous molecules from the solid or liquid sample. In one embodiment, the solid/liquid sample system 34 can be an extraction device that utilizes steam distillation to remove the molecules from the solid/liquid sample 37 that has been inserted into the solid/liquid sample system 34. As shown in FIG. 4, the solid/liquid sample system 34 can have a water supply 39 separated from the solid/liquid sample 37 by a membrane 38. Upon rapidly heating the water present in the water supply 39 to generate steam, the steam flows from the water supply 39 through the porous membrane (the membrane 38 provides barrier to liquid water but not to steam) into the sample bed with the solid/liquid sample 37. The steam can saturate the solid/liquid sample 37 and distill the molecules from the solid/liquid sample. The pump 22 can then be used to flow the steam from the sample bed into the sample collecting devices 24, so the sample collecting devices 24 can trap the molecules from the solid/liquid sample 37 as described above. While the embodiment of FIG. 3 shows a solid/liquid sample system 34 coupled to the sample collecting devices 24, it is to be understood that other embodiments of the odor processing device 20 may not include a solid/liquid sample system 34 and the odor processing device 20 would only be able to collect and process air-based odors.

The odor processing device 20 may also include a power supply 25 to provide energy to one or more components (e.g., pump 24, desorption device 26, etc.) of the odor processing device 20. In one embodiment, the power supply 25 may have an interface that allows the power supply 25 to plug into or otherwise interface with an external component, such as a wall outlet or battery, and receive electrical power from such external component. In another embodiment, the power supply 25 may incorporate one or more batteries (e.g., a lithium-ion battery, lithium-polymer battery, nickel-cadmium battery, or nickel-metal-hydride battery) to permit the odor processing device 20 to be independent of the external power component. Power supply 25 may include a charging interface such as a physical connector to attach to a charger or inductive charging circuitry.

Referring back to FIG. 2, after the separated molecules are provided to the sniff port 30 of the odor processing device 20 (sometime referred to as a series of odor notes), the user 40 can enter olfactory information regarding the sniffed molecules into the hand-held computing device 60 (step 214). In one embodiment, the hand-held computing device 60 can be a smartphone. However, in other embodiments, the hand-held computing device 60 can be a personal digital assistant (PDA), tablet computer, portable gaming device, and/or an attachable, wearable, implantable or non-invasive computer or device.

Figure 5:
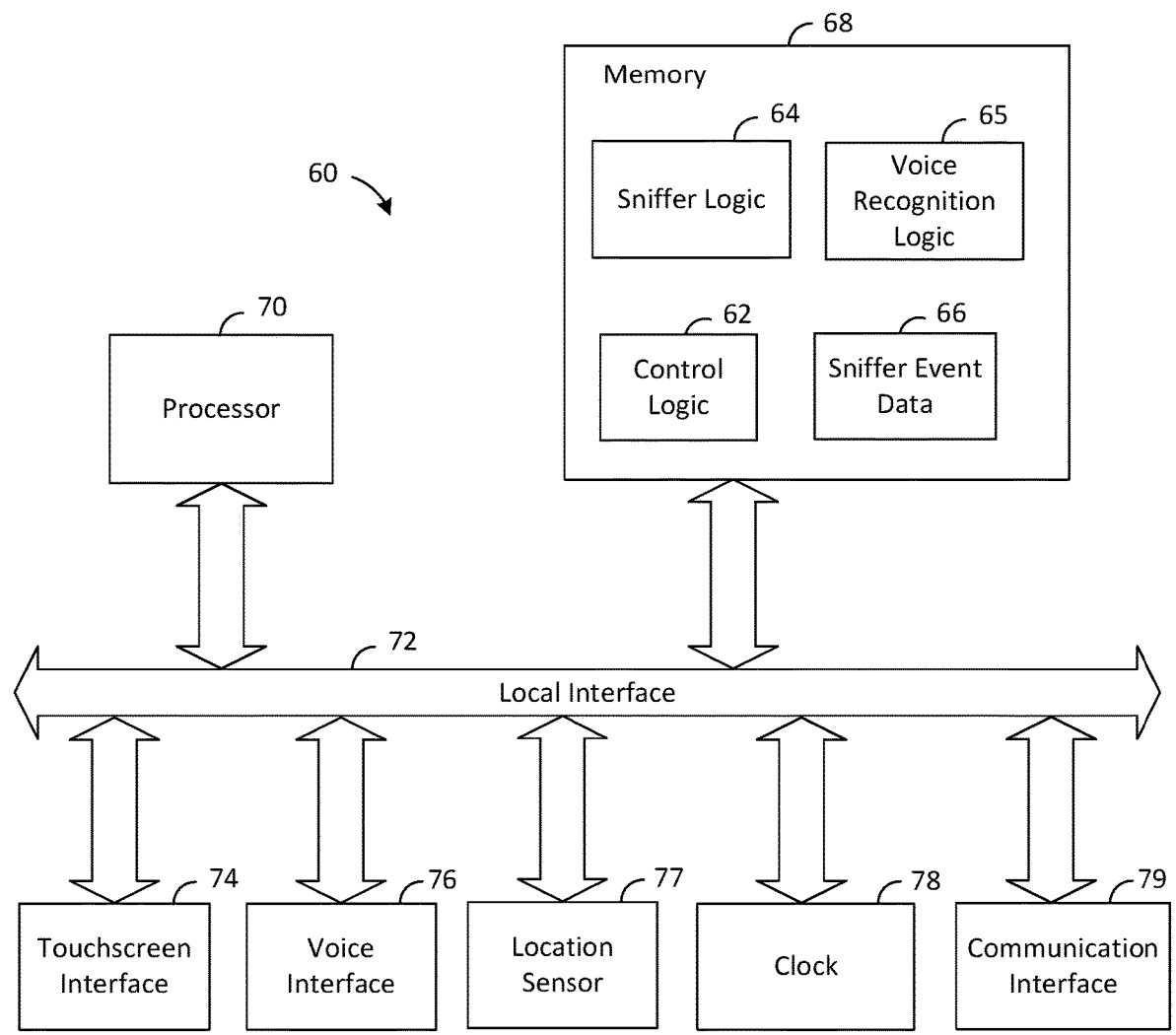
FIG. 5 shows a block diagram of an embodiment of an hand-held computing device from the system of FIG. 1.

FIG. 5 shows an embodiment of the hand-held computing device 60 of the system 100. The hand-held computing device 60 may include logic 62, referred to herein as "control logic," for generally controlling the operation of the hand-held computing device 60. The hand-held computing device 60 also includes sniffer logic 64 to collect, store, process and analyze the sniffer event data 66 and to identify the molecules present in the sample collected by the odor processing device 20. The hand-held computing device 60 can also include voice recognition logic 65 to convert voice entries provided by the user 40 to the voice interface 76 into text that can be stored as sniffer event data 66. The control logic 62, the sniffer logic 64 and the voice recognition logic 65 can be implemented in software, hardware, firmware or any combination thereof. In one embodiment, the sniffer logic 64 can generate a molecule intensity and duration measurement display (e.g., an aromagram) that includes the text of the voice entries provided by the voice recognition logic 65. In addition, the sniffer logic 64 can be used to perform the analysis associated with identifying the sniffed molecules and to control the timing and/or data transfer between the hand-held computing device 60 and the odor processing device 20 and its corresponding components.

In the hand-held computing device 60 shown in FIG. 5, the control logic 62, the sniffer logic 64 and the voice recognition logic 65 are implemented in software and stored in memory 68 of the hand-held computing device 60. Note that the control logic 62, the sniffer logic 64 and the voice recognition logic 65, when implemented in software, can be stored and transported on any non-transitory computer-readable medium for use by or in connection with an instruction execution apparatus (e.g., a microprocessor) that can fetch and execute instructions. In the context of this application, a "computer-readable medium" can be any device, system or technique that can contain or store a computer program for use by or in connection with an instruction execution apparatus. The hand-held computing device 60 may be implemented as a combination of hardware and software, such as at least one microprocessor or other type of processor programmed with instructions for performing various functions. Other configurations of the hand-held computing device 60 are possible in other embodiments.

The hand-held computing device 60 shown in FIG. 5 includes at least one processor 70, which has processing hardware for executing instructions stored in memory 68. As an example, the processor 70 may include a digital signal processor or a central processing unit (CPU). The processor 70 communicates to and drives the other elements within the hand-held computing device 60 via a local interface 72, which can include at least one bus. Furthermore, a touchscreen interface 74 can be used to input data from the user 40 into the hand-held computing device 60. In one embodiment, the touchscreen interface 74 can include a touchscreen that may be used to display images to the user 40 and also to receive inputs from the user 40. Similarly, the voice interface 76 can be used to receive voice or audio entries from the user 40. In one embodiment, the voice interface 76 can include a microphone to record sound or noise occurring in the area surrounding or in proximity to the hand-held computing device 60.

The hand-held computing device 60 can also include a location sensor 77 (e.g., a GPS (global positioning system) sensor) to provide information relating to the location of the hand-held computing device 60 and a clock 78 that can be used to track time and synchronize operations within the hand-held computing device 60. The clock can also be used to provide a time stamp on the user's entries (either voice or touch) into the hand-held computing device 60 to indicate when the sniffer event data 66 was obtained. In one embodiment, the control logic 62 and/or the sniffer logic 64 can determine the user's location using information from the location sensor 77 and store this information with the user's entries (either voice or touch) into the hand-held computing device 60 to indicate where the sniffer event data 66 was obtained. In another embodiment, voice interface 76 may include circuitry for receiving electrical signals representative of voice entries or other audio information from user 40, and may include circuitry for providing electrical or data signals representing voice entries or audio information to voice recognition logic 65.

Hand-held computing device 60 may also include a communication interface 79. Communication interface 79 may be a wired interface, wireless interface, or any combination thereof. A wired interface of communication interface 79 may include a receptacle to interface with a wired connection and communication circuitry for sending and receiving data over a suitable wired connection (e.g., Ethernet, USB, FireWire, lightning, etc.). A wireless interface of communication interface 79 may include a wireless transceiver and related circuitry for transmitting and receiving data over any suitable wireless interface (e.g., Wi-Fi, Bluetooth, cellular, NFC, etc.). In one embodiment, the communication interface 79 can include a radio frequency (RF) radio or other device for communicating wirelessly with the odor processing device 20, the network 80 and server computers 90. The communication interface 79 can be used to receive information from the odor processing device 20 (e.g., an analysis from detector 36) in one embodiment. The received information from the odor processing device 20 can be stored in sniffer event data 66 and then processed by the sniffer logic 64 as needed.

Hand-held computing device 60 can also include an input interface (not shown) that can enable the user to enter information into the hand-held computing device 60 via other techniques besides voice and touch input. For example, the input interface may permit data entry by one or more of the following: keyboard, mouse, pen, gestures, virtual reality, augmented reality, etc.

Figure 6:
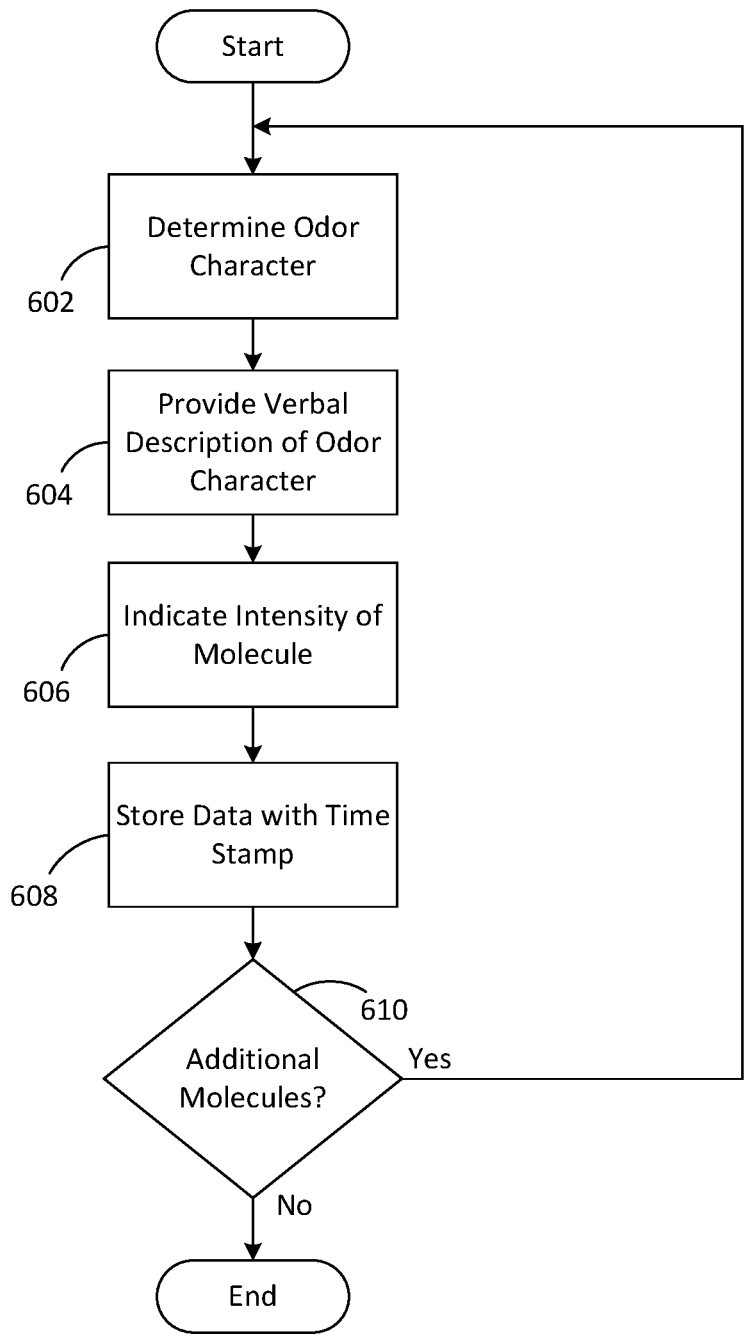
FIG. 6 is a flowchart showing an embodiment of a process for the user to enter olfactory information into the hand-held computing device.
Figure 7:
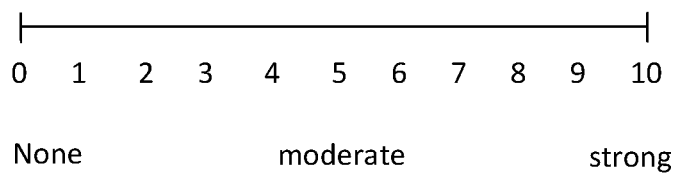
FIG. 7 shows a front view of an input screen of the touchscreen interface for entering olfactory information.

FIG. 6 is a flow chart showing an embodiment of a process for a user 40 to enter olfactory information regarding a molecule (or odor note) sniffed by the user 40 from the sniff port 30. In one embodiment, the user 40 can enter olfactory information via a time-intensity olfactory assessment system (or other olfactory assessment system) provided by the sniffer logic 64. The time-intensity olfactory assessment system enables the entry of real-time intensity vs. time measurement information (e.g., retention time) along with an odor descriptor for the molecules received by voice recognition logic 65. The olfactory information entered by the user 40 can then be used for the identification of the molecules associated with the odor at the location. In one embodiment, the process of FIG. 6 can be used to enter olfactory information in step 214 of the process of FIG. 2.

The process begins with the user 40 sniffing for a group of molecules from the sniff port 30 (sometimes referred to as an odor note) and determining the odor character of the sniffed molecules (step 602). The user 40 can then provide a verbal description of the odor character of the sniffed molecules to the hand-held computing device 60 via voice interface 76 (step 604). In other words, when the user 40 perceives a molecule at the sniff port 30, the odor character of the molecule is verbally described by the user 40 and recorded by the voice interface 75. The voice interface can then provide the recorded description to the voice recognition logic 65 present in the hand-held computing device 60 for conversion to a text form and storage in sniffer event data 66.

Figure 8:
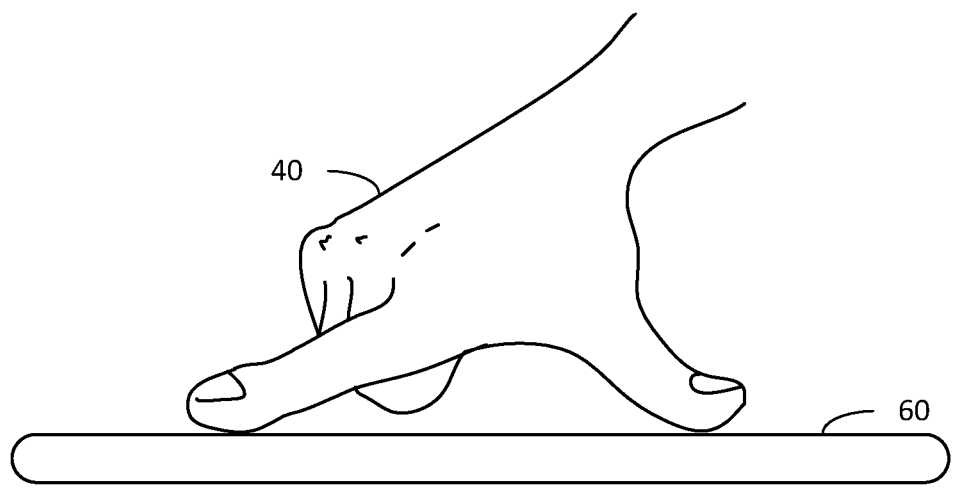
FIG. 8 shows a side view of a user entering olfactory information into the hand-held computing device.
Figure 9:
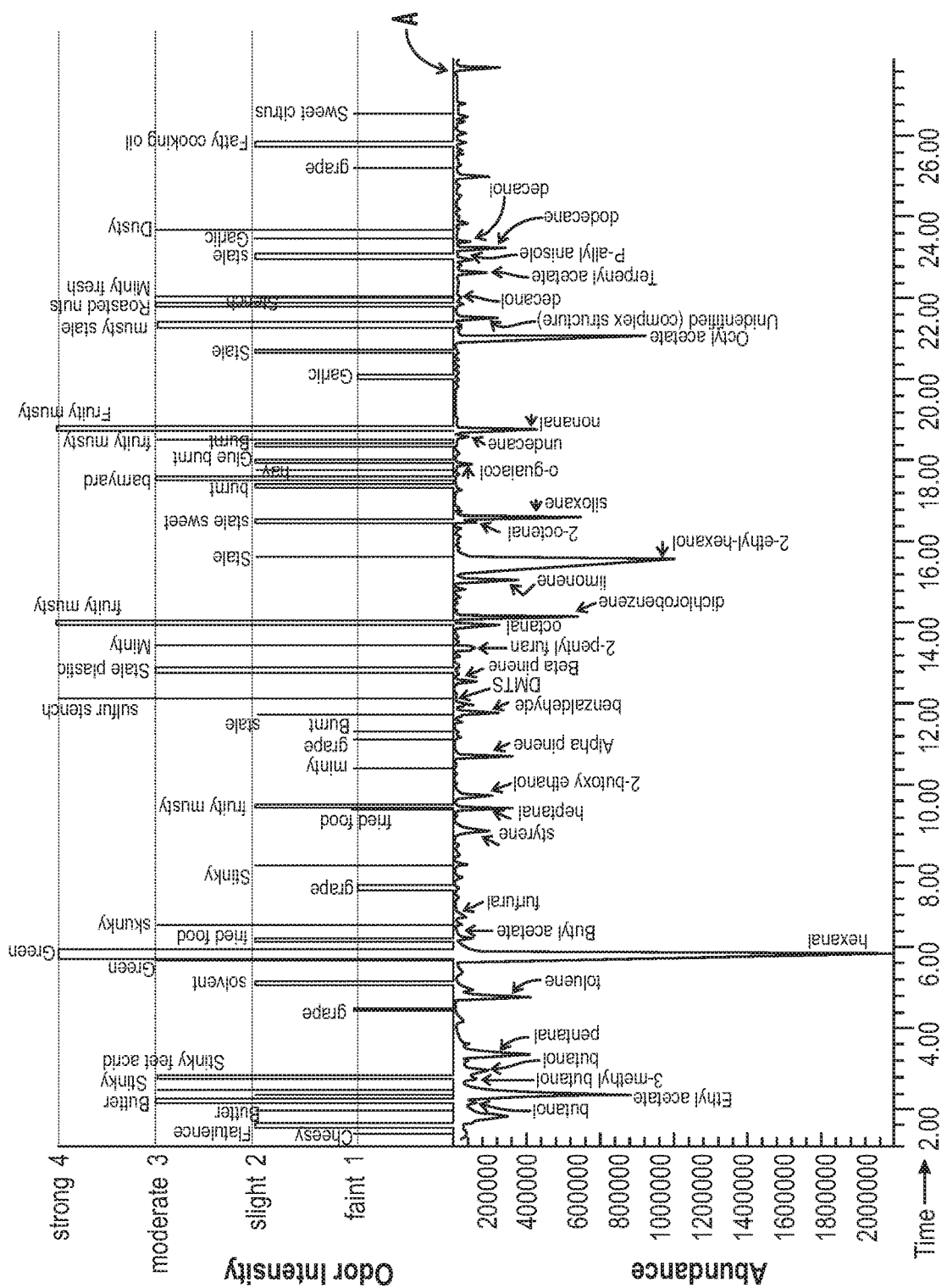
FIG. 9 shows an embodiment of a graph with aromagram information and chromatography information.

The user 40 can then indicate the intensity and duration of the sniffed molecules via the touchscreen interface 74 of the hand-held computing device 60 (step 606). FIG. 8 shows an embodiment of a user interface on the touchscreen interface 74 that is generated by the sniffer logic 64 for the user to interact with to enter the intensity and duration of the molecules from the sniff port 30. In one embodiment, the user can enter and/or adjust the intensity associated with the molecules from the sniff port 30 via a touch input by sliding either a finger of thumb of the user along touchscreen interface 74 as shown by FIG. 9. In one embodiment, the intensity of the molecules from the sniff port 30 can be indicated with the user's fingers (e.g., thumb and index finger) by adjusting the distance between the fingers as the fingers imprint on the touchscreen interface 74 of the hand-held computing device 60. In one embodiment, the user 40 inputs the duration of the odor note by pressing his/her fingers to the touchscreen interface 74 for the amount of time that the odor is detected. The providing of the duration information by the user 40 can occur simultaneously with the providing of the intensity data by the user 40. In other words, the duration of the odor note can correspond to the time the user 40 begins entering intensity data for the odor note (e.g., touches touchscreen interface 74 with finger) and the time the user 40 stops entering intensity data (e.g., removes finger from touchscreen interface 74). The touchscreen interface 74 can provide tactile feedback to the user 40. The distance indicated between the user's fingers can be correlated with a 0-10 point sensory scale (see FIG. 8). The widest distance (based on the physical size of the touchscreen interface 74 of the hand-held computing device 60) that can be indicated by the user 40 is equal to an intensity of ten (10), or strong odor associated with the sniffed molecules. A distance between the user's fingers equal to one-half the size of the touchscreen interface 74 indicates an intensity of five (5), or moderate odor associated with the sniffed molecules. No distance between the user's fingers on the touchscreen interface 74 can indicate an intensity of zero (0) no odor was detected from the sniffed molecules. The method of measuring odor intensity with cross-modal matching of aroma intensity and linear distance perception using the touchscreen interface 74 and the sniffer logic 64 can improve the accuracy of the intensity determination by the user 40.

In one embodiment, a time parameter that can be used to calculate a retention time for the sniffed molecules (or odor note) can be determined to correspond to the time when the user 40 enters an initial intensity for the sniffed molecules. In another embodiment, a time duration of the sniffed molecules (or odor note) from the sniff port 30 can correspond to the time between the first non-zero indication of intensity for the sniffed molecules until the intensity of the sniffed molecules is adjusted to zero. The time parameter and/or retention time and the time duration, if determined, can be stored in sniffer event data 66 with the other olfactory information pertaining the sniffed molecules.

The verbal description of the molecule and the indicated intensity of the molecule provided by the user 40 can be time stamped by clock 79 and stored in sniffer event data 66. In one embodiment, the verbal description of the molecule and the indicated intensity of the molecule provided by the user can also be stored with location data from location sensor 77. Once the user-provided verbal description and the indicated intensity of the molecule from the sniff port 30 is stored, a determination can be made as to whether additional molecules are being provided from the sniff port 30 (step 610). If there are no further molecules being provided from the sniff port 30, the process can end. However, if additional molecules are provided from the sniff port 30, the process can restart with the user 40 determining the odor character of other sniffed molecules in step 602.

Referring back to FIG. 2, once the information regarding the sniffed molecules has been entered in step 214, an aromagram can be generated on the hand-held device 60 for the user 40 (step 216). The aromagram can include the retention time, odor intensity data, and odor duration data for the sniffed molecules on a 2-dimensional graphical display plot. In one embodiment, if a detector 36 is also used in the odor processing device 20, the information displayed by the aromagram can be synchronized (e.g., using a start signal) with the retention time vs signal intensity/duration data generated by the detector 36 (if present) so that signals match based on retention times. FIG. 9 shows an embodiment of an aromagram displaying both information entered by the user 40 and information provided by the detector 36. In FIG. 9, the information above the horizontal axis (A) can be provided by the user 40 and the information below the horizontal axis (A) can be provided by the detector 36. As can be seen in FIG. 9, there is a substantial correlation of the two sets of information in that several of the peaks identified by the detector 36 correspond directly to peaks identified by the user 40. This correspondence of information can provide a level of assurance to the user 40 that the user's assessment of the molecules is correct.

The sniffer logic 64 can then use the information from the aromagram to calculate a retention index for each of the sniffed molecules (step 218). The retention index is a value that is calculated in order to reliably compare the results from different systems (e.g., gas chromatographs) and to account for differences in the operation of the systems. The retention index can be calculated based on a calibration parameter that is determined for the particular system (e.g., desorption device 26 and separator 28) using one of two mixtures (e.g., a solution of linear hydrocarbons ("HC Standard") or a solution of linear ethyl esters ("Ester Standard")). The retention index can be a system-independent constant that corresponds to a retention time for a sniffed molecule. The retention time for a sniffed molecule can correspond to the time taken for a molecule to pass through separator 28 (e.g., a chromatography column). The retention time can be calculated as the time from injection of the molecule into the separator 28 to the detection of the molecule at the sniff port 30.

The sniffer logic 64 can then generate a table (or other data structure) that correlates the calculated retention indexes for the sniffed molecules with the olfactory information from the user 40 and, if used, the detector information from detector 36 (step 220). After generating the table, the sniffer logic can then access the databases at the server computers 90 to obtain information from the databases that lists identified molecules based on the molecule's retention index and other olfactory information and/or detector information (step 222). The sniffer logic 64 can then identify the molecules in the table using the information obtained from the databases (step 224). In one embodiment, the sniffer logic 64 can compare the retention indexes for the molecules in the table to determine if there is a substantial correlation with a retention index for an identified molecule in the database. If there is a substantial correlation, the sniffer logic can determine that the molecule from the table is the identified molecule from the database. The sniffer logic 64 can then determine if the olfactory information and/or detector information for the molecule in the table is substantially similar to the corresponding information for the identified molecule in the database in order to confirm the identification. If there is no substantial correlation of retention indexes between a molecule in the table and the molecules in the database or if the olfactory information and/or detection information of the molecule in the table and an identified molecule in the database does not correspond, the molecule is not identified. In one embodiment, the sniffer logic 64 can automatically generate a report for the user 40 on the hand-held computing device 60 that includes the identified molecules and the olfactory information for the identified molecules. If a detector 36 is included in the odor processing device 20, the report can also include the information generated by the detector 36.

The user 40 can then compare the identified molecules from the sniffer logic 64 to the preliminary odor profile generated by the user 40 at the start of the process (step 226). Based on the comparison, the user 40 can then determine if a good sample was collected (step 228). If the user 40 determines that a good sample has not been collected (e.g., the preliminary odor profile has only limited correspondence with the identified molecules), the process returns to step 206 to collect additional samples and repeat the process. However, if there is substantial correspondence between the preliminary odor profile prepared by the user and the identified molecules from the sniffer logic, the user 40 can confirm that a good sample has been collected and can send the second sample to a laboratory for further analysis (step 230). When sending the second sample collecting device 24 to the laboratory for further analysis, the user 40 can remove the second sample collecting device 24 and place the sample collecting device in a sealed vessel (e.g., a sealed aluminum foil envelope or a glass jar) that prevents the second sample collecting device 24 (or sorbent material) from being further exposed to chemicals. In another embodiment, the second sample collecting device 24 can be placed in the sealed vessel prior to initiating the processing of the first sample collecting device 24.

At the laboratory, a desorption process is then applied to the second sample collecting device 24 to desorb (or remove) the molecules extracted and concentrated by the second sample collecting device 24. The molecules absorbed and/or adsorbed by the sorbent material of the second sample collecting device 24 may be desorbed by any method including thermal desorption, solvent desorption, or desorption by exposure to different energy sources, including various forms of electromagnetic energies. For thermal desorption, the sorbent material is placed in a thermal desorption unit or heated chamber, equipped with inert gas flushing and temperature control. Upon heating the chamber, molecules desorb from the sorbent material, are swept by an inert gas or other gas (e.g., helium, nitrogen, argon, hydrogen) into a trap mechanism (e.g., a liquid nitrogen cooled cryo-trap, an absorbent material, or a combination thereof). The trap mechanism may be rapidly heated to release components and deposit them as a tight band on a capillary column for separation by a gas chromatograph (GC) and detection and measurement by a detector (e.g., mass spectrometer (MS), flame ionization, or flame photometric). Alternatively, the molecules may be desorbed by solvent and analyzed by GC or by high performance liquid chromatography (HPLC). HPLC may utilize various detectors, such as MS, infrared (IR), ultraviolet (UV), diode array, and/or other wavelength of electromagnetic radiation. In one embodiment, the analysis performed by the laboratory can provide similar results to the detector information generated by the detector 36.

A report can then be generated by the laboratory with the results of the analysis and provided to the user 40. In one embodiment, the presentation of the data can use an automated graphical presentation on the hand-held computing device 60. In another embodiment, an automated report system can be used where the identification of the molecules and the olfactory information collected by the sniffer logic 64 can be combined with the results of the analysis from the laboratory and transmitted to the user 40 with minimal manual labor.

Although the figures herein may show a specific order of method steps, the order of the steps may differ from what is depicted. Also, two or more steps may be performed concurrently or with partial concurrence. Variations in step performance can depend on the software and hardware systems chosen and on designer choice. All such variations are within the scope of the application. Software implementations could be accomplished with standard programming techniques, with rule based logic and other logic (such as machine learning) to accomplish the various connection steps, processing steps, comparison steps and decision steps.

It should be understood that the identified embodiments are offered by way of example only. Other substitutions, modifications, changes and omissions may be made in the design, operating conditions and arrangement of the embodiments without departing from the scope of the present application. Accordingly, the present application is not limited to a particular embodiment, but extends to various modifications that nevertheless fall within the scope of the application. It should also be understood that the phraseology and terminology employed herein is for the purpose of description only and should not be regarded as limiting.

What is claimed is:

1. An odor analysis system to identify odors present at a location, the system comprising:
    an odor processing device positioned at the location and configured to collect at least two samples having molecules associated with the odors at the location, the odor processing device configured to process one sample of the at least two samples to provide a plurality of odor notes to a user, each odor note of the plurality of odor notes corresponds to a type of molecule; and
    a computing device configured to be carried by the user at the location, the computing device comprising a voice interface to record a verbal description of an odor note of the plurality odor notes spoken by the user and a touchscreen interface to receive a touch input from the user corresponding to an intensity and duration of the odor note of the plurality of odor notes, the computing device configured to determine a retention time for the odor note of the plurality of odor notes and to calculate a retention index for the odor note of the plurality of odor notes based on the determined retention time, the computing device further configured to identify, at the location, the type of molecule associated with the odor note of the plurality of odor notes based on the retention index and information obtained over a network from a server computer, wherein the obtained information corresponds to an identified molecule and a corresponding retention index for the identified molecule.

2. The system of claim 1, wherein the computing device is configured to generate an aromagam for the user based on the verbal description, intensity and duration provided by the user for each odor note of the plurality of odor notes.

3. The system of claim 1, wherein the computing device is configured to enable a user to prepare a preliminary odor profile of the odors at the location prior to the odor processing device collecting the at least two samples.

4. The system of claim 3, wherein a second sample of the at least two samples is analyzed by a laboratory in response to the preliminary odor profile prepared by the user corresponding to the identified molecules from the computing device.

5. The system of claim 1, wherein the odor processing device comprises a gas chromatograph.

6. The system of claim 1, wherein the odor processing device comprises a detector configured to analyze the plurality of odor notes.

7. The system of claim 1, wherein the touch input received by the touchscreen interface corresponds to the user adjusting a distance between two fingers of the user.

8. The system of claim 1, wherein the computing device is configured to correlate the verbal description of an odor note of the plurality odor notes with the intensity of the odor note of the plurality of odor notes.

* * * * *